United States Patent [19]

Weir

[11] Patent Number: 5,239,483
[45] Date of Patent: Aug. 24, 1993

[54] DETECTION OF CHEMICALS

[75] Inventor: Donald J. Weir, London, England

[73] Assignee: The General Electric Company, p.l.c., England

[21] Appl. No.: 621,797

[22] Filed: Dec. 4, 1990

[30] Foreign Application Priority Data

Dec. 6, 1989 [GB] United Kingdom ............... 8927567

[51] Int. Cl.$^5$ .................................. G06F 15/46
[52] U.S. Cl. ................................ 364/497; 73/23.35; 364/499
[58] Field of Search ............... 364/496, 497, 498, 499, 364/500; 395/906, 914, 932; 73/23.35

[56] References Cited

U.S. PATENT DOCUMENTS

| | | | |
|---|---|---|---|
| 4,365,303 | 12/1982 | Hannah et al. | 364/498 |
| 4,586,143 | 4/1986 | Kaneyasu et al. | 364/497 X |
| 4,638,443 | 1/1987 | Kaneyasu et al. | 364/497 |
| 4,703,646 | 11/1987 | Muller et al. | 73/23 |
| 4,766,551 | 8/1988 | Begley | 364/498 |
| 4,818,348 | 4/1989 | Stetter | 364/497 X |
| 4,847,783 | 7/1989 | Grace et al. | 364/497 |
| 4,958,295 | 9/1990 | Davidson et al. | 364/497 |
| 5,106,756 | 4/1992 | Zaromb | 364/498 X |

FOREIGN PATENT DOCUMENTS 2203249 10/1988 United Kingdom .
9008314 7/1990 World Int. Prop. O. .

OTHER PUBLICATIONS

Electronics and Wireless World, Feb. 1989, pp. 178-180; "Intelligent Odour Discriminating Nose".
Analytical Chemistry, vol. 59, No. 11, Jun. 1987, pp. 1529-1534, Washington, D.C., W. P. Carey et al., "Multicomponent analysis using an array of piezoelectric crystal sensors".
Sensors and Actuators, vol. 18, No. 3/4, Jul. 1989, pp. 291-296, Lausanne, Switzerland; K. Ema et al, "Odour-sensing system using a quartz-resonator sensor array and neural-network pattern recognition".

Primary Examiner—Kevin J. Teska
Attorney, Agent, or Firm—Kirschstein, Ottinger, Israel & Schiffmiller

[57] ABSTRACT

A device for detecting the presence of a chemical material, such as a gas, amongst a number of incident chemical materials comprises a group of sensors having overlapping broadband selectivities in respect of the incident materials, so that each sensor responds, to a greater or smaller extent, to each of the materials. The sensor outputs are fed to a signal processor which produces, for each material, a notional vector. These vectors are compared with stored reference vectors to identify the material under investigation. The responses to the various materials have a time-varying portion and a portion of constant value. Certain materials may produce the same constant value, but different time-varying portions. The latter portions are therefore also taken into account in identifying the materials. A chromatographic layer may be provided over the sensors to distinguish between chemical species in the materials under test.

6 Claims, 3 Drawing Sheets

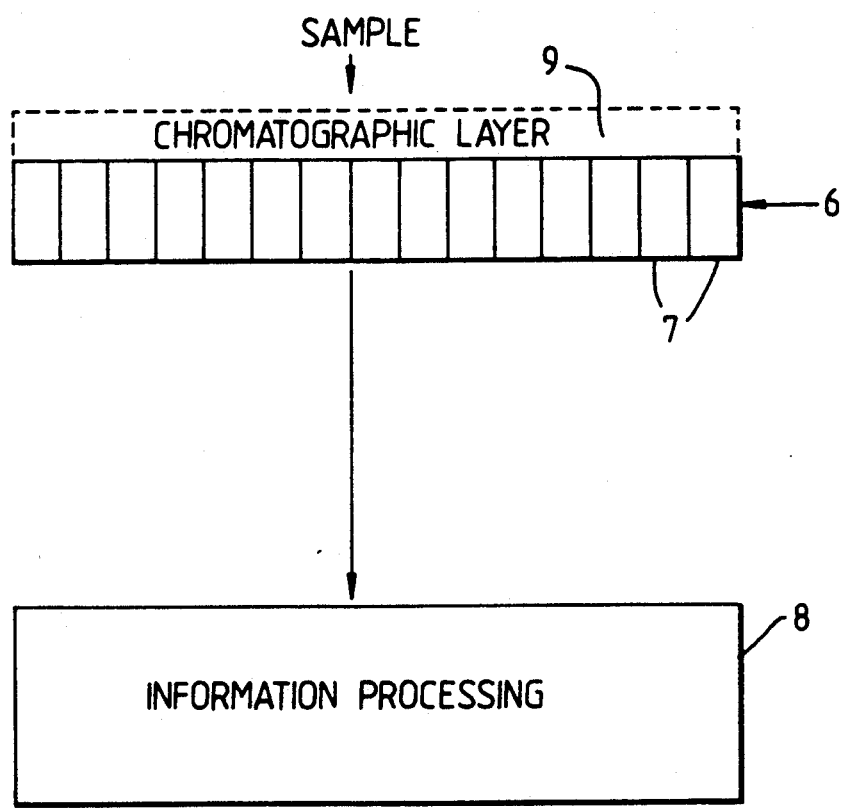

DETECTION OF CHEMICALS

BACKGROUND OF THE INVENTION

1. Field of the Invention

This invention relates to the detection of chemicals, and particularly to a device for detecting the presence of specific chemical materials, more especially, but not exclusively, gases, amongst a plurality of chemical materials.

2. Description of Related Art

Although there have long been in existence devices, such as pellistors, which can detect the presence of a specific material, such a device cannot detect individually, with the same high sensitivity, a number of such materials.

More recently, devices have been proposed which use an array of sensors, each of which is primarily sensitive to a particular chemical material. The primary material is different for each sensor, but the sensors have overlapping broadband selectivity characteristics, so that each sensor responds differently from the others to all of the materials under test. Each sensor provides electrical outputs corresponding, respectively, to each of the materials. Corresponding outputs of all of the sensors are fed to information processing means, which determines from the signals provided by the corresponding outputs a "feature vector" which represents the material. From a comparison of this feature vector with such vectors of known substances the particular material is identified. Similar information processing is effected for each of the sets of corresponding outputs from the sensors, enabling identification of the other materials within the operating range of the sensors.

In such known devices the information processing is effected on the basis of the responses of the detectors once they have reached a state in which their outputs are steady, but a number of different materials may give rise to the same sensor responses.

SUMMARY OF THE INVENTION

It is an object of the present invention to provide an improved chemical detector using such an array of broadband detectors.

According to the invention there is provided a detection device for detecting the presence of chemical materials individually amongst a plurality of chemical materials, comprising a group of sensors each operative to produce outputs representing time-varying concentration characteristics of each of a number of chemical materials, the sensors having mutually different selectivities in relation to those chemical materials; and processing means operative to receive from all of the detectors the outputs corresponding to a sensed material, operative to produce therefrom a representation of that material comprising a vector and an analysis of both the steady state and the temporal dynamics of the detector outputs for that material, and operative to compare said vector and said analysis with stored data representing reference materials for identification of the sensed material.

BRIEF DESCRIPTION OF THE DRAWINGS

Embodiment of the invention will now be described, by way of example, with the reference to the accompanying drawings, in which

FIG. 6 shows, schematically, an alternative embodiment of the invention.

DETAILED DESCRIPTION OF THE PREFERRED EMBODIMENTS

Figure 1:
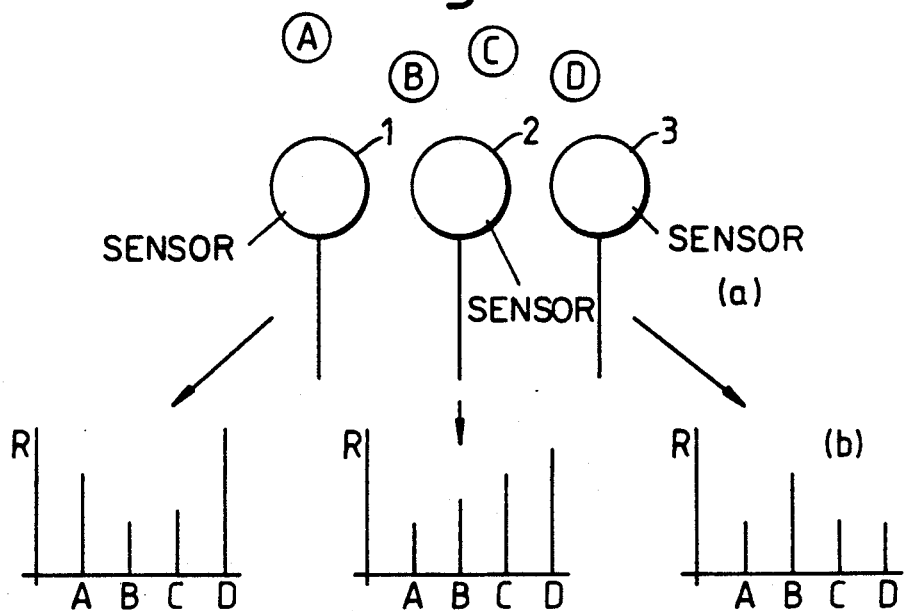
FIG. 1 represents, schematically, outputs obtained from a group of sensors in response to the sensing of a plurality of chemical materials.

Referring to FIG. 1($a$) of the drawings, a detector comprises a number of sensor of which, for the sake of example, three sensors 1, 2 and 3 are shown. The detector may, however, comprise many more such sensors. The sensors have broadband selectivity in respect of a number of incident chemical materials, such as materials A,B,C and D, the bands for the individual sensors being mutually displaced but overlapping so that each sensor responds, to a greater or lesser extent, to each of the materials. FIG. 1($b$) represents, schematically, the respective responses (R) of the sensors 1, 2 and 3 to the individual materials A-D.

Figure 2:
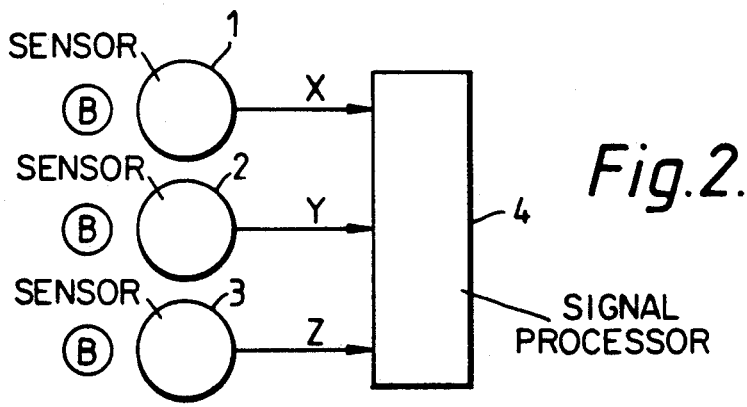
FIG. 2 represents, schematically, outputs from the sensors resulting from the sensing of one of the materials.
Figure 3:
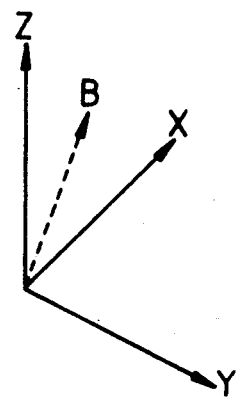
FIG. 3 is a schematic vector representation of the sensor outputs of FIG. 2.

Outputs, designated X, Y and Z, of the sensors 1, 2 and 3, respectively, resulting from one of the chemical materials (shown as the material B in FIG. 2) are fed to a signal processor 4. The processor 4 notionally generates a vector (FIG. 3) representing the material B as the resultant of the outputs X, Y and Z. This vector may be considered as a "fingerprint" for the material.

The vector is then compared with a stored set of reference vectors which have been previously obtained by calibration of known materials. In this way the particular material may be identified.

The sensors will produce further sets of outputs corresponding to the materials A, C and D and these will similarly be operated on by the processor 4.

The concentration of a chemical material in a sample under investigation will be represented by the length of its vector as compared with the length of the vector obtained for a standard sample. This relies on a consistent, i.e. linear, response of the sensors to variations in the concentration. Hence, the ratio of responses must remain constant. Furthermore, the response of the sensors to a mixture of chemical materials must be equal to the sum of their responses to the components of the mixture. Some types of sensor exhibit this linear behavior, but others do not. The processor 4 must then operate in a non-linear manner to compensate for the deficiencies of the latter sensors.

Figure 4:
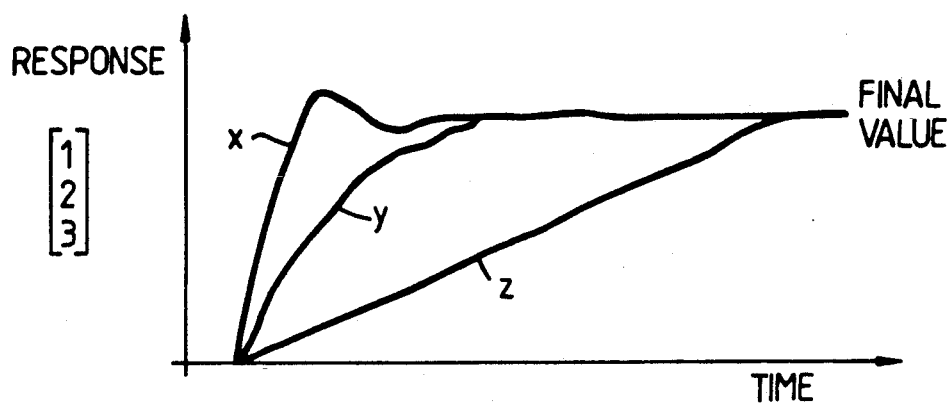
FIG. 4 is a graph of sensor response against time for three different chemical materials.

The operation of the device as so far described is the same as that of the previously-proposed sensor array devices. However, as mentioned above, such devices take into account only the steady-state responses of the sensors. FIG. 4 shows that the responses of three different chemical materials can reach the same steady state value and therefore produce the same steady state vector, so that the prior devices would not distinguish between those materials.

Figure 5:
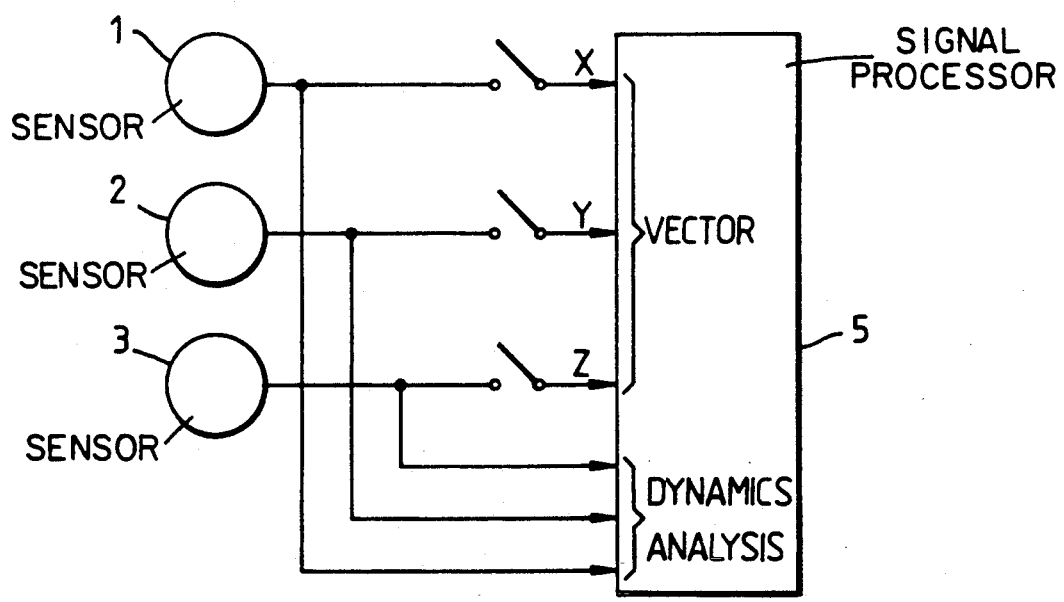
FIG. 5 shows an extension of FIG. 2 in accordance with the present invention.

However, it will be seen that the responses vary widely from one material to another during their rise to the steady state condition, i.e. in the time-varying portion x, y or z of the characteristic. In the present invention, a processor 5 (FIG. 5) additionally analyses these variations, and makes use of the analysis, together with the steady state vectors, to distinguish between the chemical materials.

Further enhancement of the discrimination of the device is obtained in an alternative embodiment as shown in FIG. 6. Here, the detection device comprises an array 6 of sensors 7 similar to those described above, coupled to a processor 8 which determines time-dependent feature vectors representing the chemicals. In addition, a chromatographic layer 9 is provided over the sensor array 6 to distinguish between chemical species in the materials under test. The layer 9 may be a silicon gas chromatograph layer. The layer may be a layer of, for example, squalane formed over the sensors 7.

The sensors 1-3 and 7 may comprise, for example, in relation to gas detection, electro-active polymers, coated surface acoustic wave devices, coated piezoelectric crystal devices or Taguchi gas detectors. An example of a suitable coating is ethyl cellulose. Alternatively, by suitable choice of the sensors, chemical materials in the liquid phase may be detected.

The vector analysis (processor 5) may be carried out by a dedicated microprocessor which will effect serial processing of the signals from the sensors. Alternatively, the signals may be processed in a parallel mode by a neural network. The use of linear nets, perceptrons, multi-layer perceptrons, Hopfield nets or neural nets is envisaged.

A device in accordance with the invention would have many applications, for example in process control in the food processing, brewing and perfumery industries, for medical diagnosis, for monitoring storage facilities and for analyzing the exhaust gas from internal combustion engines.

The detection is effected in a manner somewhat akin to the olfactory function of human and other mammals.

I claim:

1. A detection device for detecting materials individually among a plurality of chemical materials, the device comprising: a group of sensors, each operative for producing time varying output signals representing time concentration characteristics of each of a number of the chemical materials, the sensors having mutually different selectivities in relation to those chemical materials; a chromatographic layer through which the chemical materials pass to reach the sensors, the chromatographic layer being common to all of the sensors; and processing means operative for receiving from all of the sensors the output signals corresponding to a sensed material, said processing means being operative for producing from said output signals a representation of that material, the representation comprising a vector and an analysis of both steady state and temporal dynamics of the sensors output signals for that material, said processing means also being operative for comparing said vector and said analysis with stored data representing reference materials, for identification of the sensed material.

2. A device as claimed in claim 1, wherein the processing means comprises a microprocessor.

3. A device as claimed in claim 1, wherein the processing means comprises a neural network.

4. A device as claimed in claim 1, wherein the sensors are surface acoustic wave devices.

5. A device as claimed in claim 1, wherein the sensors comprise electro-active polymer materials.

6. A device as claimed in claim 1, wherein the sensors comprise Taguchi gas detectors.

* * * * *